United States Patent [19]

Drake

[11] Patent Number: 4,686,182
[45] Date of Patent: Aug. 11, 1987

[54] METHOD AND KIT FOR DETECTING ANTIBIOTICS IN A LIQUID SAMPLE

[75] Inventor: James F. Drake, Minneapolis, Minn.

[73] Assignee: Minnesota Mining and Manufacturing Company, St. Paul, Minn.

[21] Appl. No.: 661,661

[22] Filed: Oct. 17, 1984

[51] Int. Cl.$^4$ .......................... C12Q 1/36; C12Q 1/38; C12Q 1/02
[52] U.S. Cl. ........................................ 435/24; 435/23; 435/28; 435/29; 435/810; 435/25; 436/23
[58] Field of Search .............................. 435/18, 23–25, 435/28, 29, 32, 810, 184; 436/23

[56] References Cited

U.S. PATENT DOCUMENTS

| | | |
|---|---|---|
| 4,239,745 | 12/1980 | Charm . |
| 4,239,852 | 12/1980 | Charm . |
| 4,331,761 | 5/1982 | Dawson et al. ................ 435/188 |
| 4,427,632 | 1/1984 | Okaniwa et al. ............... 435/14 X |
| 4,442,204 | 4/1984 | Greenquist et al. ........... 436/530 X |
| 4,546,076 | 10/1985 | Degelaen et al. .............. 435/180 X |
| 4,555,484 | 11/1985 | LaRossa et al. ................ 435/21 |

FOREIGN PATENT DOCUMENTS 2008248  5/1979  United Kingdom .

OTHER PUBLICATIONS

Frère, J. et al, *Biochem J.,* vol. 143, 1974, pp. 233–240.
*Chemical Abstracts,* vol. 90, No. 25, 1979, p. 227, #199525m, Frère, J. M. et al, "The Exocellular . . . with β-Lactam Antibiotics".
*Chemical Abstracts,* vol. 85, No. 23, 1976, p. 180, #173261u, Marquet, A. et al, "Membrane-Bound . . . β-Lactam Antibiotics".
*Chemical Abstracts,* vol. 87, No. 7, 1977, p. 73, #48470b, "Interactions between . . . *Streptococcus Faecalis,* ATCC 9790".
*Chemical Abstracts,* vol. 83, No. 17, 1975, p. 199, Abstract No. 143667x, Kawashima, K. et al.
Frere, J. et al, "Enzymatic Method for Rapid and Sensitive Determination of β-Lactam Antibiotics", *Antimicrobial Agents and Chemotherapy,* vol. 18, No. 4, Oct. 1980, pp. 506–510.
Fuad, N. et al, *Biochemical J.,* vol. 155, 1976, pp. 623–629.

*Primary Examiner*—Sidney Marantz
*Assistant Examiner*—Jeremy M. Jay
*Attorney, Agent, or Firm*—Donald M. Sell; James A. Smith; Mary M. Allen

[57] ABSTRACT

A method of detecting a beta-lactam antibiotic in a liquid sample comprising the steps of: (a) forming a reaction medium by adding the sample to a predetermined amount of a dry reagent formulation comprising a D,D-carboxypeptidase, a substrate for said D,D-carboxypeptidase containing a carboxy-terminal D-alanine, and a reagent system which produces a color change in the presence of D-alanine; (b) incubating said reaction medium for a predetermined period; (c) adding a quenching material to terminate the reaction; (d) observing the color of the reaction medium. A kit for carrying out this method is also disclosed.

12 Claims, No Drawings

METHOD AND KIT FOR DETECTING ANTIBIOTICS IN A LIQUID SAMPLE

FIELD OF THE INVENTION

This invention relates to an improved enzymatic method for the detection of beta lactam antibiotics in a liquid sample such as milk. More particularly, it relates to an improved assay for beta lactam antibiotics based on the ability of such antibiotics to bind with and inactivate D,D-carboxypeptidase.

BACKGROUND ART

Antibiotic contamination of milk following treatment of dairy cows for mastitis or other infections is a major problem in the dairy industry. Beta lactam antibiotics (e.g., penicillins and cephalosporins) are the most common of such contaminants.

Each year, large quantities of milk must be discarded due to antibiotic contamination. Additional economic losses result from the need to recall contaminated milk products and the disruption of milk processing, such as cheese or yoghurt culturing, due to antibiotics in milk.

A substantial portion of the loss due to antibiotic contamination could be avoided if a simple, fast assay for antibiotics in milk could be made at the dairy farm before pickup of the milk by the milk hauler. Detection of contaminated milk at this very early point would prevent contamination of larger quantities of uncontaminated milk in the milk haulers truck and at the milk receiving station.

The current official method for detection of antibiotics in milk relies on the inhibition of bacterial growth by antibiotics. These growth-based assays require a minimum of $2\frac{1}{2}$ to 3 hours to complete. They are not practical as a means of detecting contaminated milk at the level of the dairy farm or even at the milk receiving station prior to transferring the milk from the hauler's truck to a storage facility.

Several rapid methods have been developed for detecting beta lactam antibiotics in milk. U.S. Pat. Nos. 4,239,745 and 4,239,852 (Charm) describe a rapid method for detecting an antibiotic in a liquid sample based on the competitive binding of the antibiotic contaminant in the sample and a tagged antibiotic to receptor sites on bacterial cells. The commercially-available version of the Charm test requires the use of expensive equipment and a trained operator.

Other proposed rapid assays for antibiotics in milk and other liquids are based on immunochemical reaction and utilize antibodies directed against specific beta-lactam antibiotics. The disadvantages of these assays include (a) the detection of immunochemical reactions requires pretreatment of the sample to remove interfering materials, (b) a mixture of antibodies with specificities for different beta lactam antibiotics is required, (c) rapid detection at 5 to 30 parts per billion requires high affinity, rapidly reacting antibody preparations that are difficult to acquire.

Frere et al ("Enzymatic Method for Rapid and Sensitive Determination of B-Lactam Antibiotics" *Antimicrobial Agents and Chemotherapy*, October 1980 p. 506–510) describe a rapid enzymatic assay for beta-lactam antibiotics which makes use of the ability of these antibiotics to inactivate a specific D,D-carboxypeptidase produced by the bacterium Actinomadura-R39. Other bacterial D,D-carboxypeptidases are known to be reversibly inhibited by beta-lactam antibiotics, but the R39 enzyme is preferred in that the rate of inactivation is very rapid and the reversal of inhibition is very slow. Thus, over short periods of time, exposure of R39 enzyme to a beta-lactam antibiotic results in a stoichiometric loss of R39 catalytic activity. Measurement of remaining R39 activity after exposure to test samples suspected of containing a beta-lactam antibiotic provides a rapid sensitive assay for the antibiotic.

The assay as described by Frere et al is similar to a commercial test known as Penzym TM sold by UCB Bioproducts, Brussels, Belgium. It is rather time-consuming and involves a number of steps and separate reagents. The first step involves an incubation, e.g., five minutes, of the test sample with the carboxypeptidase. If the test sample contains a beta-lactam antibiotic, a certain amount of the enzyme will be inactivated during the incubation depending on the amount of antibiotic present.

The next step involves the addition of a substrate for the carboxypeptidase which is a peptide containing a carboxyterminal D-alanine. This is followed by another incubation (e.g., 15 minutes) during which D-alanine is released from the substrate. Other reagents are added during this incubation period to measure the amount of D-alanine liberated. The liberated D-alanine is oxidized into pyruvic acid by a D-amino acid oxidase enzyme with simultaneous formation of hydrogen peroxide. The hydrogen peroxide oxidizes an organic redox indicator, e.g., o-dianisidine, which provides a colorimetric readout. Sulfuric acid is added at the end of the incubation period to terminate the reaction and stabilize the color formation. The Penzym TM kit is supplied with seven separate reagents including: (1) the D,D-carboxypeptidase; (2) buffer for the D,D-carboxypeptidase; (3) substrate for the D,D-carboxypeptidase ((Acetyl)$_2$-L-Lys-D-ala-D-ala); (4) flavin adenine dinucleotide, cofactor of the D-amino acid oxidase; (5) peroxidase; (6) o-dianisidine and (7) D-amino acid oxidase.

The Penzym TM assay suffers from a number of disadvantages. Firstly, the sequential addition of reagents in several different steps is required. Secondly, the amount of time required to complete the assay, i.e., 20 to 30 minutes, is considered excessive, particularly by milk haulers. Furthermore, an excessive number of separately-packaged reagents must be handled.

BRIEF SUMMARY OF THE INVENTION

The present invention overcomes the aforementioned disadvantages and provides an improved method for detecting beta-lactam antibiotics in a liquid sample consisting essentially of the steps of:

(1) forming a reaction medium by adding the liquid sample to a predetermined amount of a combination of dry reagents comprising a D,D-carboxypeptidase, a substrate for the D,D-carboxypeptidase containing a carboxyterminal D-alanine, and a reagent system which produces a color reaction in the presence of D-alanine; and (2) incubating in the range of about 20° to 60° C. for a predetermined period of time; (3) adding a material which quenches the color-producing reaction and (4) examining the color of the reaction medium. Preferably the reagent system which results in a color reaction in the presence of D-alanine comprises a D-amino acid oxidase, a cofactor for D-amino acid oxidase, peroxidase and an organic redox indicator, e.g., o-dianisidine, which undergoes a color change when oxidized.

The present invention also provides a reagent kit for detecting beta-lactam antibiotics in a liquid sample comprising a predetermined amount of dry reagents comprising D,D-carboxypeptidase, a substrate for the D,D-carboxypeptidase containing a carboxyterminal D-alanine, and a reagent system which produces a color reaction in the presence of D-alanine, said dry reagents being carried on a solid substrate which can be contacted with the liquid sample in one step.

The method of the present invention is capable of detecting concentrations of beta-lactam antibiotics above about 0.03 micrograms per milliliter of liquid sample. It was surprising that such sensitivity could be achieved without incubating the D,D-carboxypeptidase with the test sample prior to adding the other reagents. The method can be carried out in as little as five minutes and all of the reagents (except for the quenching material) are added at one time.

The minimum equipment necessary to carry out the method is a device to maintain a constant temperature such as an oven, electric crockpot or, preferably, a small incubator. The method utilizes a minimum number of steps and a combination reagent package which permits all assay reagents to be added simultaneously. The method is extremely simple and rapid, especially suited to the dairy farmer or the milk hauler.

DETAILED DESCRIPTION

In order to detect specific minimum amounts of beta-lactam antibiotics, a known amount of D,D-carboxypeptidase enzyme must be used. In order to detect a concentration of greater than $5 \times 10^{-8}$ moles/liter of beta-lactam antibiotic such as Penicillin G in a test sample to which all of the assay reagents are added simultaneously, it is necessary to provide at least about $2 \times 10^{-8}$ moles per liter of enzyme. The enzyme, carried on a substrate along with the other reagents used in the assay, is combined with the liquid test sample to be assayed. Preferably, the test sample is added to the dry reagents. These reagents, other than the carboxypeptidase, are generally present in sufficient excess so as not to limit or appreciably slow the color-producing reaction. On the other hand, large excesses should be avoided, since these reagents are expensive, and large excesses may have a negative effect on the assay.

For speed, it is preferred that the assay be carried out at the highest temperature possible without inactivating the reagents. The optimum temperature is approximately 50° C. The assay can be run at lower temperatures, but reaction time is much longer and below about 20° C., enzyme activity is too low to be readily detected.

The preferred D,D-carboxypeptidase for use in the assay of the present invention is available from UCB Biochemicals, Brussels, Belgium. As noted above, this enzyme is produced by the microorganism *Actinomadura R39*. The R39 enzyme is a water-soluble protein having a molecular weight of 53,000.

The substrate for the carboxypeptidase may be any of a number of peptides whose structure includes a carboxyterminal D-alanine. Examples of suitable substrates are described by Ghuysen et al., Ann. Rev. Biochem., 48, p. 73-101 (1979). A preferred substrate is N,N-diacetyl-L-lysyl-D-alanyl-D-alanine. Especially preferred is the monoacetyl tripeptide, N-acetyl-L-lysyl-D-alanyl-D-alanine, which is hydrolyzed at nearly twice the rate of the diacetyl tripeptide. The amount of substrate added to the sample is preferably in the range of 1.0 to 3.0 mg/ml final concentration.

The reagent system which produces a color change in the presence of D-alanine preferably includes D-amino acid oxidase which oxidatively deaminates D-alanine to produce pyruvate, ammonia and hydrogen peroxide. A cofactor, flavin adenine dinucleotide (FAD), is necessary to the activity of D-amino acid oxidase. The D-amino acid oxidase and FAD are preferably present in an amount ranging from 0.20 to 2.0 IU/ml and 0.01 to 0.15 mg/ml, respectively.

The peroxide generated from D-alanine is used to oxidize a colorless precursor to a colored species in a reaction catalyzed by the enzyme peroxidase. Peroxidase, e.g., horseradish peroxidase such as that commercially available from Sigma Chemical Company, is included in the reagent system in an amount ranging from 0.01 to 0.05 mg/ml.

Examples of dyes which react with peroxide to provide a color change include dicarboxidine (gamma, gamma-4,4'-diamino-3,3'-biphenylenedioxy)dibutyric acid), ortho-dianisidine, 4-amino-antipyrrole plus phenol, ortho-phenylenediamine, toluidine and the like. Dicarboxidine and ortho-dianisidine are preferred dyes. The dye is preferably present in an amount between 0.1 and 0.5 mg/ml.

In order to terminate the color producing reaction of the assay, an acid which will lower the pH of the reaction medium below about pH 4.0 is required. Strong inorganic acids such as sulfuric, hydrochloric, phosphoric and the like readily accomplish the lowering of the pH. If dicarboxidine or orthoanisidine is used as the dye, the addition of sulfuric acid to a final concentration of about 25% by volume provides an enhancement of color in addition to stopping the reaction. It may be desirable to use an acid in dry form, e.g., tablet, for convenient use. For this purpose an acid such as sulfamic acid or $H_3AsO_4$ may be used. Of course, the acid which terminates the assay reaction cannot be a component of the assay reagent package and must be provided separately.

The dry mixture of reagents may be provided in alternative formulations. In one simple embodiment a tube contains the dried reagents as several spots on the inside surface, each of which has been applied to the tube as a solution and dried to provide a solid residue. Each reagent may be added separately, or in some cases two or more reagents may be parts of the same solution.

In another variation, the mixture of reagents is supplied, absorbed and dried on a fiber web of inert, non-cellulosic material as disclosed in copending application Ser. No. 661,662 filed on even date herewith, the disclosure of which is incorporated herein by reference.

The mixture of reagents is applied, for example, in solution to the web by any suitable and convenient method which permits a quantitative or at least semi-quantitative measure of the amount of reagents per unit volume of web. The web may be pre-cut into units of a desired size and configuration, or it may be loaded with the reagent mixture and then cut or divided into units of a desired size and/or configuration. Suitable methods for applying the reagents may be automated, semiautomated or manual. Manual methods include pouring, pipetting and spraying. Preferably, the reagents are applied to a dry, non-woven fibrous web which has been pretreated with a small amount, for example, 0.01 to 5% by weight, of a surfactant to facilitate wetting of the web. The surfactant may be cationic, anionic or nonionic, and is preferably inert with respect to the reagents involved. For most web materials, it is necessary to use a surfactant in order to obtain adequate wetting and spreading of the reagent solutions. With some materials (such as polyamide) which are slightly polar, some wetting is obtained without surfactant.

Suitable fibrous webs for use according to the present invention are prepared by methods known in the art. Non-woven webs may be prepared by melt-blowing as is known to those skilled in the art and described in, for example, U.S. Pat. No. 3,978,185 and Y. A. Wente et al. "Manufacture of Superfine Organic Fibers", Naval Research Laboratories Report No. 4364, Naval Research Laboratories, Washington, D.C. (U.S. Document No. 111437). Alternative techniques such as solution-blowing can also be used as described, for example, in U.S. Pat. No. 2,571,457. The method used to prepare the non-woven material is not critical.

The materials useful in preparing suitable fibrous webs include polymers and copolymers of monomers which form fibrous webs. Suitable polymers include polyalkylenes such as polyethylene, polybutylene and polypropylene; polyvinyl chloride; polyamides such as the various nylons; polystyrene, polyarylsulfones; polyesters such as poly(ethylene terephthalate); and polyurethanes such as polyether polyurethanes. Webs may also be prepared from combinations of co-extruded polymers such as polyester and polyalkylenes. Copolymers of these polymers may also be used. Webs may also be combined with webs which are an intimate blend of fine fibers and crimped staple fibers.

The structure of materials useful as fibrous substrates for the dry reagents may be quite varied. Non-woven, microfibrous webs are preferred. Non-woven webs have several advantages over woven materials including ease of manufacture, lower material cost, allowance for variation in fiber texture and fiber density, and greater surface area for carrying more reagents.

As used herein, the term "non-woven fibrous web" means a sheet or pad of a non-woven network of fibers. The term "microfiber" means a filament structure having an average fiber diameter of less than 20 microns, preferably below about 10 microns, and the term "filament" means a fiber of at least 60 cm in length.

In order to obtain dry formulations of the assay reagents, the reagents are dissolved or suspended in aqueous solution, the solution is applied to the web, followed by evaporation of the solvent. Evaporation may be carried out by simple air-drying, evaporation in vacuo or lyophilization. The formulations obtained are stable, i.e., they retain their enzymatic activity, at ambient conditions for hours or even days, e.g., up to 2 weeks. If stability of weeks or months is desired, it is preferred to protect the formulations from atmospheric moisture and heat. Such protection will include separating the formulation into a dry atmosphere or packaging in paper, plastic or metal foil containers or pouches. Temperature protection may include refrigeration or freezing. Refrigerated packages will retain stability and provide reliable tests for at least 9 months.

The invention may be further illustrated by the following non-limiting examples:

EXAMPLE 1

Formulation of D,D-carboxypeptidase on a Nonwoven Web and Its Activity

Microfibrous web samples (polypropylene treated with about 1% of Aerosol OT ® Surfactant obtained from American Cyanamid Co., Wayne, N.J.), each sample measuring ⅛ inch by ¼ inch and weighing about 3.5 to 4.0 mg, were saturated with reagents obtained form a commercially available Penzym ® kit (UCB Biochemicals, Brussels, Belgium). Each of five web samples was saturated with 5 microliters of a solution prepared by reconstituting a vial from the Penzym ® kit containing D,D-carboxypeptidase and HEPES buffer with 500 microliters of water. The moist webs were lyophilized to dryness and stored desiccated at 4° C. Six ¼ inch web squares (treated with surfactant as noted above) were saturated with 5 microliters of a solution prepared by reconstituting a vial from the Penzym ® kit containing N,N-diacetyl-L-lysyl-D-alanyl-D-alanine and ortho-dianisidine with 500 microliters of water and 10 microliters of a suspension from a Penzym ® vial containing D-amino acid oxidase, peroxidase and flavin adenine dinucleotide. The moist webs were lyophilized and stored desiccated at 4° C.

Solutions of Penicillin G in whole milk at concentrations of 0.1; 0.05; 0.03 and 0.01 units of Penicillin G per milliliter were prepared.

All tests were run by reacting for fifteen minutes at 50° C., then measuring the color obtained. A blank assay was run with 50 microliters of a pure milk sample plus a web containing dry D,D-carboxypeptidase and buffer and a web containing all of the other essential components of the assay. A dark pink color was obtained indicating the presence of D-alanine and the absence of any beta-lactam antibiotic.

A blank assay was run with 50 microliters of a pure milk sample plus a web containing all of the essential components of the assay except D,D-carboxypeptidase. No color developed (as expected) since an essential component of the assay was missing.

A group of assays was run using each of the milk solutions of Penicillin G prepared above. Fifty microliters of each milk solution was reacted with a pair of webs containing all of the essential components of the assay. (i.e., one web containing the D,D-carboxypeptidase and buffer, the other web containing the remaining reagents.) Pink colors were obtained for concentrations of Penicillin G of 0.01 and 0.03 units per millileter, indicating the assay was not sensitive to these low concentrations. No color was obtained at concentrations of Penicillin G of 0.05 and 0.10 units per milliliter, indicating the presence of Penicillin G.

All of the essential ingredients including the D,D-carboxypeptidase may be coated on a single web. However, reaction of the enzyme with its substrate must be minimized. This requires careful handling of the reagents. In the recommended procedure, all reagents except the D,D-carboxypeptidase are coated on the web, which is then lyophilized. Thereafter, the D,D-carboxypeptidase is added, preferably to the back side of the web relative to the other reagents, and the web cooled as rapidly as possible to −40° C. or colder for lyophilization

EXAMPLE 2

A set of 10 clear polystyrene tubes (12×75 mm) was prepared for use in a beta-lactam antibiotic assay. Stock solutions of
(A) D,D-carboxypeptidase (R-39, UCB Biochemicals), $5 \times 10^{-7}$ moles per liter
(B) N,N-diacetyl-L-lysyl-D-alanyl-D-alanine, 20 mg per ml (C) ortho-dianisidine, 5 mg per ml (D) flavin adenine dinucleotide, 1.25 mg per ml (0.40 ml); D-amino acid oxidase, 5 mg per ml ammonium sulfate suspension, Sigma Chemical Company (0.10 ml); and peroxidase, 6.6 mg per ml ammonium sulfate suspension, Sigma Chemical Company (0.25 ml) and (E) trishydroxymethylaminomethane, 60 mg per ml (0.5 M), Sigma Chemical Company were used.

To each tube were added separate drops of 4.5 microliters of (A), 3.7 microliters of (B), 2.8 microliters of (C), 5.0 microliters of (D) and 2.0 microliters of (E). The tubes were then frozen for one hour at −40° F. and dried and lyophilized for two hours at 25° F. Each tube was then capped and stored in a cold (4° C) desiccator.

Aqueous solutions of Penicillin G at concentrations of 1.0, 0.60 and 0.20 units (1 unit=0.6 micrograms of the sodium salt) per milliliter were prepared. Each of these solutions was then diluted with milk to yield solutions with concentrations of 0.05, 0.03 and 0.01 units per milliliter in milk.

Assays were carried out on each of the concentrations, comparing the pure milk as a blank. The assays were carried out using the tubes containing dried assay reagents prepared above. To each tube was added 50 microliters of a given concentration of milk, the tube was shaken by hand for 0.5 minute then incubated at 50° C. for 10 minutes. Fifty microliters of 50% aqueous sulfuric acid was then added to stop the reaction. The results are shown below:

TABLE I

| Concentration of Penicillin G (units/ml) | Pink Color | Presence of Penicillin |
|---|---|---|
| 0.05 | No | + |
| 0.03 | Slight | ± |
| 0.01 | Yes | − |
| 0.00 (blank) | Yes | − |

What is claimed is:

1. A method of detecting a beta-lactam antibiotic in a liquid sample comprising:
    a. forming a reaction medium by adding said sample to a predetermined amount of a dry reagent formulation comprising a D,D-carboxypeptidase, a substrate for said D,D-carboxypeptidase containing a carboxyterminal D-alanine, and a reagent system which produces a color change in the presence of D-alanine;
    b. incubating said reaction medium for a predetermined period;
    c. adding a quenching material to terminate the reaction;
    d. observing the color of the reaction medium.

2. The method according to claim 1 wherein said liquid sample is milk.

3. The method according to claim 1 wherein said D,D-carboxypeptidase is that obtained from Actinomadura strain R39.

4. The method according to claim 1 wherein said substrate for said D,D-carboxypeptidase is selected from the group consisting of N,N-diacetyl-L-lysyl-D-alanyl-D-alanine and N-acetyl-L-lysyl-D-alanyl-D-alanine.

5. The method according to claim 1 wherein said reagent system which produces a color change in the presence of D-alanine comprises D-amino acid oxidase, a cofactor for D-amino acid oxidase, peroxidase and a dye which changes from a colorless to a colored species in the presence of peroxide.

6. The method according to claim 5 wherein said cofactor is flavin adenine dinucleotide.

7. The method according to claim 5 wherein said dye is selected from the group consisting of o-dianisidine and dicarboxidine.

8. The method according to claim 1 wherein said quenching material is sulfuric acid.

9. A kit for detecting beta-lactam antibiotics in milk comprising a solid substrate carrying a single dry reagent formulation comprising predetermined amounts of a D,D-carboxypeptidase, a substrate for said carboxypeptidase containing a carboxyterminal D-alanine, and a reagent system which produces a color change in the presence of D-alanine.

10. The kit according to claim 9 wherein said reagent system which produces a color change in the presence of D-alanine comprises D-amino acid oxidase, a cofactor for D-amino acid oxidase, peroxidase and a dye which changes from a colorless to a colored species in the presence of peroxide.

11. The kit according to claim 9 wherein said substrate is a reaction vessel having said dry reagent formulation coated in discrete areas on the interior surface thereof.

12. The kit according to claim 11 wherein said vessel is a glass or plastic tube.

* * * * *